US007147665B1

(12) United States Patent
Bryan et al.

(10) Patent No.: US 7,147,665 B1
(45) Date of Patent: Dec. 12, 2006

(54) THREADED CYLINDRICAL MULTIDISCOID SINGLE OR MULTIPLE ARRAY DISC PROSTHESIS

(75) Inventors: Vincent Bryan, Mercer Island, WA (US); Alex Kunzler, LaQuinta, CA (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/744,493

(22) PCT Filed: Jul. 22, 1999

(86) PCT No.: PCT/US99/16648

§ 371 (c)(1), (2), (4) Date: Jun. 19, 2001

(87) PCT Pub. No.: WO00/04851

PCT Pub. Date: Feb. 3, 2000

(51) Int. Cl.
*A61F 2/44* (2006.01)

(52) U.S. Cl. .................................................. 623/17.16

(58) Field of Classification Search ............. 623/17.11, 623/17.12, 17.13, 17.14, 17.15, 17.16
See application file for complete search history.

(56) References Cited

U.S. PATENT DOCUMENTS 2,677,369 A 5/1954 Knowles
3,486,505 A 12/1969 Morrison
3,875,595 A 4/1975 Froning
3,876,728 A 4/1975 Stubstad
4,023,572 A 5/1977 Weigand et al.
4,116,200 A 9/1978 Braun et al.
4,179,810 A 12/1979 Kirsch
4,309,777 A 1/1982 Patil
4,349,921 A 9/1982 Kuntz
4,599,086 A 7/1986 Doty
4,645,507 A 2/1987 Engelbrecht et al.
4,714,469 A 12/1987 Kenna
4,743,256 A 5/1988 Brantigan
4,757,983 A 7/1988 Ray et al.
4,759,766 A 7/1988 Buettner-Janz et al.
4,759,769 A 7/1988 Hedman et al.
4,766,328 A 8/1988 Yang
4,777,942 A 10/1988 Frey et al.
4,800,639 A 1/1989 Frey et al.
4,834,757 A 5/1989 Brantigan
4,863,476 A * 9/1989 Shepperd ..................... 623/17
4,863,477 A 9/1989 Monson (Continued)

FOREIGN PATENT DOCUMENTS

DE 2263842 7/1974

(Continued)

OTHER PUBLICATIONS

Artificial Disc, Market Potential and Technology Update, Viscogliosi Bros., LLC, Feb. 2000, pp. 1-65.

(Continued)

*Primary Examiner*—Alvin J. Stewart
(74) *Attorney, Agent, or Firm*—Haynes and Boone, LLP

(57) ABSTRACT

A small profile, cylindrically shaped prosthetic disc device is provided. The device housing is comprised of two longitudinally split hollow halves, between which are contained multiple discoid shaped resilient bodies which may be of a polymeric type, or they may contain hydrogel. These bodies may lie in concave surfaces located on the interior of each side of the split cylindrical housing. The housing halves even under maximum physiological loads, do not contact one another directly. Threads on the exterior surface of the cylindrical housing facilitates insertion and retention in the prepared bone opening.

19 Claims, 4 Drawing Sheets

20 10 35 35 2 26 35 22 35 24 31 30 28 2

U.S. PATENT DOCUMENTS 4,874,389 A 10/1989 Downey
4,878,915 A 11/1989 Brantigan
4,887,595 A 12/1989 Heinig et al.
4,904,260 A 2/1990 Ray et al.
4,904,261 A 2/1990 Dove et al.
4,908,032 A 3/1990 Keller
4,908,036 A 3/1990 Link et al.
4,911,718 A 3/1990 Lee et al.
4,917,704 A 4/1990 Frey et al.
4,932,969 A 6/1990 Frey et al.
4,932,975 A 6/1990 Main et al.
4,946,378 A 8/1990 Hirayama et al.
4,955,908 A 9/1990 Frey et al.
4,978,355 A 12/1990 Frey et al.
4,997,432 A 3/1991 Keller
5,002,576 A 3/1991 Fuhrmann et al.
5,015,247 A 5/1991 Michelson
5,035,716 A 7/1991 Downey
5,047,055 A 9/1991 Bao et al.
5,059,193 A 10/1991 Kuslich
5,059,194 A 10/1991 Michelson
5,062,845 A 11/1991 Kuslich et al.
5,071,437 A 12/1991 Steffee
5,080,662 A 1/1992 Paul
5,084,048 A 1/1992 Jacob et al.
5,108,438 A 4/1992 Stone
5,122,130 A 6/1992 Keller
5,123,926 A 6/1992 Pisharodi
5,171,280 A 12/1992 Baumgartner
5,171,281 A 12/1992 Parsons et al.
5,176,708 A 1/1993 Frey et al.
5,192,326 A 3/1993 Bao et al.
5,192,327 A 3/1993 Brantigan
5,234,431 A 8/1993 Keller
5,236,460 A 8/1993 Barber
5,246,458 A 9/1993 Graham
5,258,031 A 11/1993 Salib et al.
5,261,911 A 11/1993 Carl
5,261,913 A 11/1993 Marnay
5,306,308 A 4/1994 Gross et al.
5,314,477 A 5/1994 Marnay
5,314,478 A 5/1994 Oka et al.
5,320,644 A 6/1994 Baumgartner
5,370,697 A 12/1994 Baumigartner
5,375,823 A * 12/1994 Navas .................... 623/17.15
5,383,933 A 1/1995 Keller
5,401,269 A 3/1995 Buttner-Janz et al.
5,403,314 A 4/1995 Currier
5,425,772 A 6/1995 Brantigan
5,425,773 A 6/1995 Boyd et al.
5,443,514 A 8/1995 Steffee
5,456,719 A 10/1995 Keller
5,458,638 A 10/1995 Kuslich et al.
5,458,642 A 10/1995 Beer et al.
5,484,437 A 1/1996 Michelson
5,489,307 A 2/1996 Kuslich et al.
5,489,308 A 2/1996 Kuslich et al.
5,496,318 A 3/1996 Howland et al.
5,507,816 A 4/1996 Bullivant
5,514,180 A 5/1996 Heggeness et al.
5,527,315 A 6/1996 Jeanson et al.
5,534,028 A 7/1996 Bao et al.
5,534,029 A 7/1996 Shima
5,534,030 A 7/1996 Navarro et al.
5,545,229 A * 8/1996 Parsons et al. .......... 623/17.15
5,549,679 A 8/1996 Kuslich
5,556,431 A 9/1996 Buttner-Janz
5,562,738 A 10/1996 Boyd et al.
5,571,189 A 11/1996 Kuslich
5,593,409 A 1/1997 Michelson
5,609,636 A 3/1997 Kohrs et al.
5,645,598 A 7/1997 Brosnahan
5,649,926 A 7/1997 Howland
5,658,285 A 8/1997 Marnay et al.
5,662,158 A 9/1997 Caldarise
5,674,294 A 10/1997 Bainville et al.
5,674,295 A 10/1997 Ray et al.
5,674,296 A * 10/1997 Bryan et al. ............. 623/17.16
5,676,701 A 10/1997 Yuan et al.
5,683,464 A 11/1997 Wagner et al.
5,702,450 A 12/1997 Bisserie
5,713,899 A 2/1998 Marnay et al.
5,716,415 A 2/1998 Steffee
5,720,748 A 2/1998 Kuslich et al.
5,722,977 A 3/1998 Wilhelmy
5,723,013 A 3/1998 Jeanson et al.
5,741,253 A 4/1998 Michelson
5,782,830 A 7/1998 Farris
5,782,832 A 7/1998 Larsen et al.
5,797,909 A 8/1998 Michelson
5,824,093 A * 10/1998 Ray et al. ..................... 623/17
5,824,094 A 10/1998 Serhan et al.
5,865,846 A 2/1999 Bryan et al.
5,865,848 A 2/1999 Baker
5,885,300 A 3/1999 Tokuhashi et al.
5,888,197 A 3/1999 Mulac et al.
5,888,226 A * 3/1999 Rogozinski .............. 623/17.16
5,897,087 A 4/1999 Farley
5,902,233 A 5/1999 Farley et al.
5,928,284 A * 7/1999 Mehdizadeh ............ 623/17.13
5,947,971 A 9/1999 Kuslich et al.
5,976,187 A 11/1999 Richelsoph
5,984,865 A 11/1999 Farley et al.
5,989,291 A 11/1999 Ralph et al.
6,001,130 A 12/1999 Bryan et al.
6,017,008 A 1/2000 Farley
6,019,792 A * 2/2000 Cauthen .................. 623/17.14
6,022,376 A 2/2000 Assell
6,033,363 A 3/2000 Farley et al.
6,059,790 A 5/2000 Sand et al.
6,059,829 A 5/2000 Schlapfer et al.
6,063,121 A 5/2000 Xavier et al.
6,066,174 A 5/2000 Farris
6,080,155 A 6/2000 Michelson
6,083,228 A 7/2000 Michelson
6,086,595 A 7/2000 Yonemura et al.
6,096,038 A 8/2000 Michelson
6,139,579 A 10/2000 Steffee et al.
6,156,067 A 12/2000 Bryan et al.
6,162,252 A 12/2000 Kuras et al.
6,179,874 B1 * 1/2001 Cauthen .................. 623/17.14
6,228,022 B1 5/2001 Friesem et al.
6,228,026 B1 5/2001 Rull et al.
6,231,609 B1 5/2001 Mehdizadeh
6,419,706 B1 * 7/2002 Graft ....................... 623/17.16

FOREIGN PATENT DOCUMENTS

DE 2804936 8/1979
DE 30 23 353 A1 4/1981
DE 37 41 493 A1 6/1989
DE 90 00 094.3 4/1990
EP 0176728 4/1986
EP 00560140 A1 9/1993
RU 895433 1/1982
RU 1560184 4/1990
WO WO 00/04839 2/2000
WO WO 00/04851 3/2000
WO WO 00/13619 3/2000

WO WO 00/13620 3/2000

OTHER PUBLICATIONS

Boning-Up, The Musculoskeletal Healthcare Industry, Industry Commentary & Review of 1999, Viscogliosi Bros., LLC, Mar. 10, 2000, pp. 1-33.
Bryan Total Cervical Disc Prosthesis, Single Level Surgical Technique Manual, SPINALdynamics Corporation, 2000, 01080-004, pp. 29.
Morphology of the Human Skeleton, pp. 268270; 283-291; 315-331; 489-495.
Spine Industry Dynamics, Viscogliosi Bros., LLC, Mar. 10, 2000, pp. 1-4.
Brain et al.; "The Neurological Manifestations of Cervical Spondylosis;" Brain: A Journal of Neurology, vol. 75; Macmillan & Co.; 1952; pp. 187-225.
Buttner-Janz et al.; "Biomechanics of the SB Charite Lumbar Intervertebral Disc Endoprosthesis;" International Orthopedics; vol. 13; 1989; pp. 173-176.
Edeland; "Some Additional Suggestions for an Intervertebral Disc Prosthesis;" Dept. of Occupational Health; Vdvo PV AB; S-40508; Goteborg; Sweden; 1985 Butterworth & Co. Publishers Ltd.
Enker et al.; "Artificial Disc Replacement;" Spine; vol. 18; No. 8; 1993; pp. 1061-1070.
Hawkins et al.; "Shear Stability of an Elastomeric Disk Spacer Within an Intervertebral Joint; A Parametric Study;" Journal of Biomechanical Engineering Technical Briefs; vol. 114; Aug. 1992; pp. 414-415.
Hedman et al.; "Design of an Intervertebral Disc Prosthesis;" Spine; vol. 17; No. 6; 1991; pp. S256-S260.
Hellier et al.; "Wear Studies for Development of an Intervertebral Disc Prosthesis;" Spine; vol. 17; No. 6 Supplement; 1992; pp. S86-S96.
Hodd; "Far Lateral Lumbar Disc Herniations;" Neurosurgery Clinics of North America; vol. 4; No. 1; Jan. 1993; pp. 117-124.
Langrana et al.; "Finite-Element Modeling of the Synthetic Intevertebral Disc;" Spine; vol. 16; No. 6: 1991; pp. S245-S252.
Lee et al.; "Development of a Prosthetic Intervertebral Disc;" Spine; vol. 16; No. 6; 1991; pp. S253-S255.
Lee et al.; "Natural History & Prognosis of Cervical Spondylosis;" British Medical Journal; Dec. 28, 1963; British Medical Association, London, England; Copyright 1963; pp. 1607-1610.
Long; "Failed Back Surgery Syndrome;" Neurosurgery Clinics of North America; vol. 2, No. 4; Oct. 1991; pp. 899-919.
Ray; "The Artificial Disc—Introduction, History and Socioeconomics;" Clinical Efficacy and Outcome in the Diagnosis and Treatment of Low Back Pain; Raven Press, Ltd., NY; 1992; pp. 205-280.
Robinson et al.; The Results of Anterior Interbody Fusion of the Cervical Spine, The Journal of Bone & Joint Surgery; vol. 44-A, No. 8, Dec. 1962; pp. 1569-1587.
Simeone and Rothman; "Cervical Disc Disease;" Pennsylvania Hospital & University of Pennsylvania; 1975; pp. 387-433.
Solini et al.; "Metal Cementless Prosthesis for Vertebral Body Replacement of Metastatic Malignant Disease of the Cervical Spine;" Journal of Spinal Disorders; vol. 2; No. 4; 1989; pp. 254-262.
Solini et al.; "Protesi Somatica Cervicale;" Ingegneria Ricostruttiva D'Avanguardia; Howmedica International; Pfizer; Italy.
Taylor, Collier; , "The Occurrence of Optic Neuritis in Lesions of the Spinal Cord, Injury, Tumor, Melitis;" Brain: A Journal of Neurology; vol. 24; Macmillian & Co. Ltd., 1901; pp. 532-550.
Tie-sheng et al.; "Lumbar Intervertebral Disc Prosthesis;" Chinese Medical Journal, 104-(5); 1991; pp. 381-386.

* cited by examiner 20
2
10
35
35
26
35
22
35

35
24
31
30
28
2
30
26
31
3
22

24
31
3
28
22
42
24

31
30
6
22
42
41
24
6

20
31
30
10
5
35
22
35
24
5

29
22
33
42
33
24
29

52
51
29
29
24

51
52
24
9
9

10
51
52
24

10

51

24

THREADED CYLINDRICAL MULTIDISCOID SINGLE OR MULTIPLE ARRAY DISC PROSTHESIS

This invention relates to the design and use of a unique disc prosthesis for the lumbar, thoracic and cervical spine. U.S. Pat. No. 5,674,296 is incorporated by reference.

BACKGROUND OF THE INVENTION

Degenerative disc disease including disc herniation may produce disabling symptoms of local pain, radiculopathy or myelopathy in an otherwise clinically stable spine, which proves to be unresponsive to non-surgical treatment. Several surgical treatments are available to address the symptoms of degenerative disc disease when non-invasive therapies are not effective. These surgical treatments include decompression, discectomy and fusion. These treatments, and in particular the discectomy and fusion procedures, provide relief of clinical symptoms but they do not restore normal or near normal range of motion or cushioning to the affected functional spinal unit (FSU). This can result in acceleration of the degenerative process in spinal discs adjacent to the original surgical operation site. This degenerative process can, in turn, require additional surgical intervention.

Open surgery and endoscopic techniques are often used to provide access to the targeted intervertebral disc space. Posterior, postero-lateral, and anterior approaches allow placement of instrumentation to facilitate exposure of the degenerated disc and the insertion of bone grafts or fusion cages to accomplish bony fusion.

Because of anatomical structure considerations and instrument size restrictions associated with minimally invasive surgical techniques in the anterior spine, the insertion of a functional disc prosthesis equal in size to the natural disc creates risks due to mechanical interferences with critical vascular structures and may prevent safe insertion of the prosthesis.

A functional disc prosthesis which provides for a full range of motion of the FSU and for cushioning between two adjacent vertebrae while maintaining stability, intervertebral body spacing and lordosis, is desirable, more specifically it is an object of the invention to provide a disc prosthesis having a small or narrow profile. The novel exemplary prosthesis is cylindrical in exterior shape, comprised of two longitudinally split halves. Each housing half is separated from the other at all times by disk shaped resilient bodies contained therein, and is strong enough to support the loads to which it shall be subjected during the activities of daily living. The housing contains multiple concave articulation recesses capable of mating with the discoid resilient bodies placed therebetween. The discoid bodies are of smaller diameter than the natural disc they replace, and are positioned in series in the shells or articulation recesses contained in the interior of the cylindrical housing. The cylindrical housing is threaded on its exterior for ease of introduction into, and mechanical stability in, a prepared space in the opposing vertebrae of the FSU. The housing is configured to fit the restrictions imposed by the limited anatomical space available for the surgical placement of the implant, and is small so as to utilize implantation procedures and instrumentation such as those used in an endoscopic procedure.

It is a further object of the invention to provide cylindrical housings of differing size, and resilient bodies contained within, so that when the cylindrically shaped prostheses units are used in parallel, they may facilitate proper positioning of opposing vertebrae.

Another object is to obviate the need for a second surgical site for bone graft harvesting.

And it is a further object of the invention to provide a sheath so as to completely surrounded and enclose the space occupied by the resilient bodies between the two cylindrical housing halves.

Still another object of the invention is to provide a disc prosthesis which will permit motion between the housing halves.

A further object of the intention is to provide a disc prosthesis which will provide for cushioning between the housing halves.

It is a still further object of the invention to provide a disc prosthesis which may be used alone or in parallel array with similar prostheses.

Other objects and advantages of the invention will become apparent to those skilled in the art upon reading the following detailed description and upon reference to the drawings. Throughout the drawings, like reference numerals refer to like parts.

While the invention will be described in connection with a preferred embodiment, it will be understood that it is not intended to limit the invention to this embodiment. On the contrary, it is intended to cover all alternatives, modifications and equivalents as may be included within the spirit and scope of the invention as defined by the appended claims.

Figures 1, 2, 3:
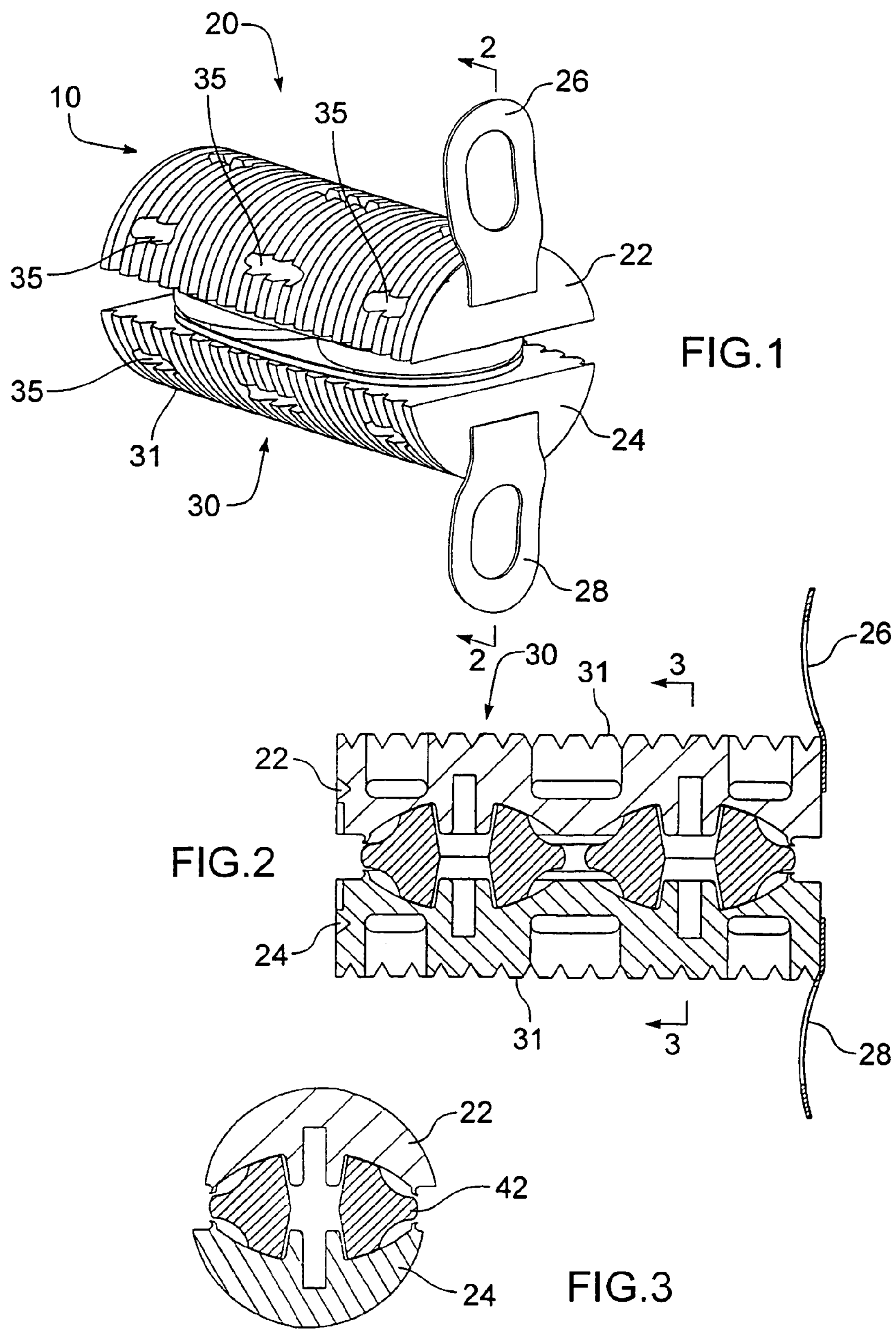
FIG. 1 is an isometric view of the novel disc prosthesis.
FIG. 2 is a sectional view taken substantially in the plane of line 2—2 in figure 1.
FIG. 3 is a sectional view taken substantially in the plane of line 3—3 in FIG. 2.
Figure 5:
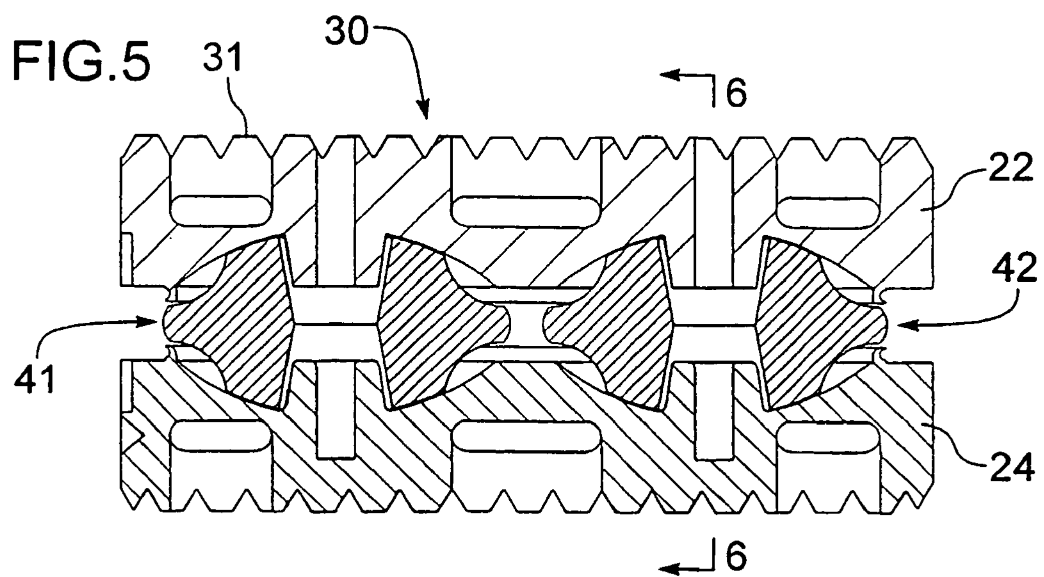
FIG. 5 is a sectional view taken substantially in the plane of line 5—5 in FIG. 4.
Figure 4:
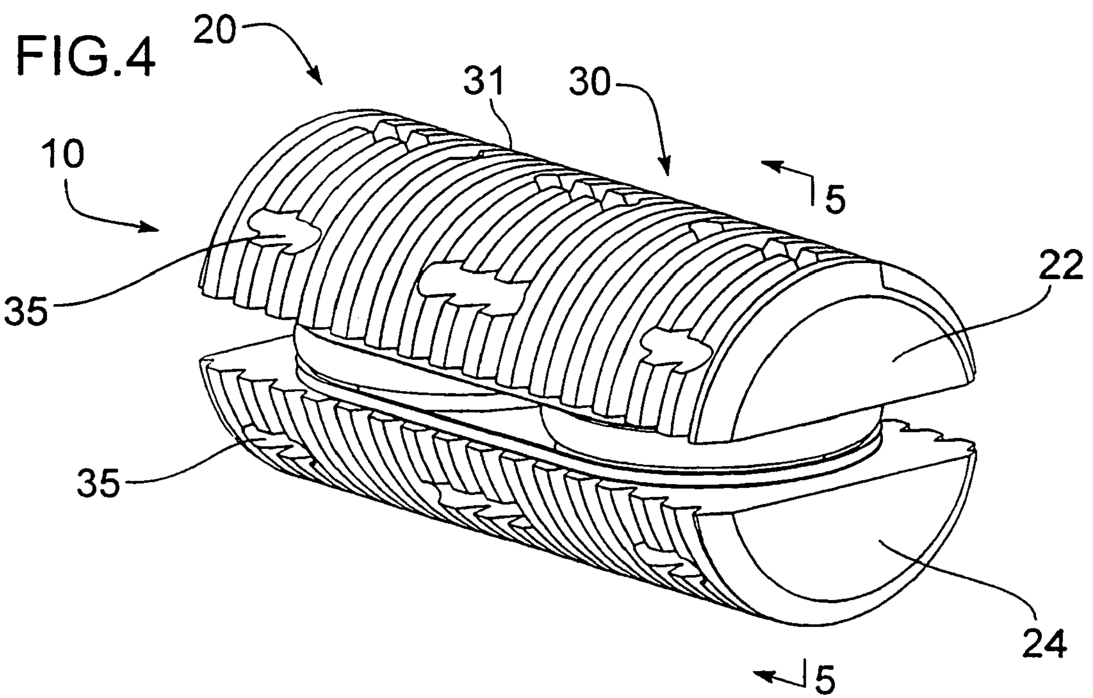
FIG. 4 is an isometric view similar to FIG. 1 but showing an alternate embodiment of the invention.
Figure 6:
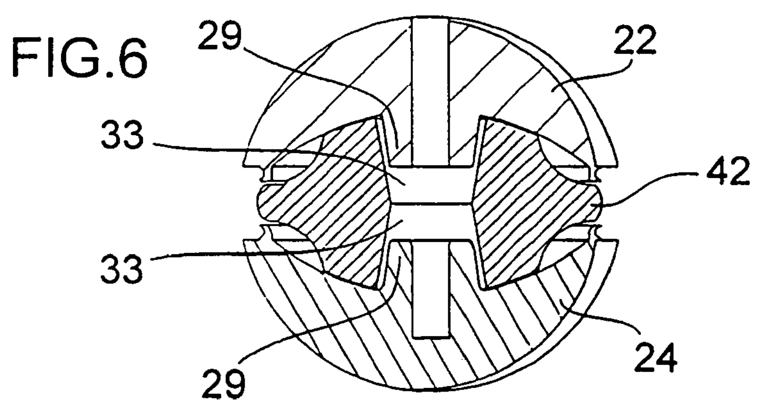
FIG. 6 is a sectional view taken substantially in the plane of line 6—6 in FIG. 5.
Figure 7:
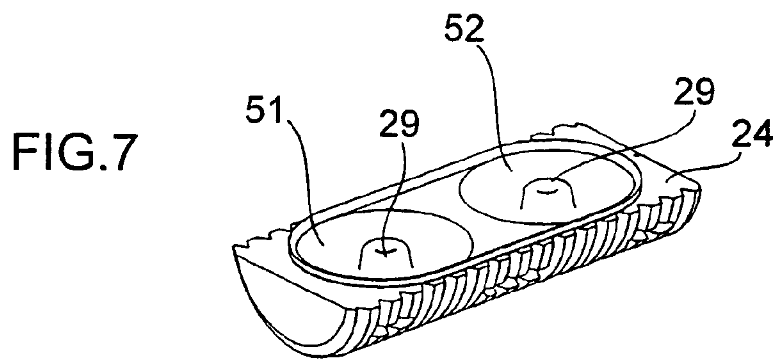
FIG. 7 is an isometric view of a lower half housing of the invention.
Figure 8:
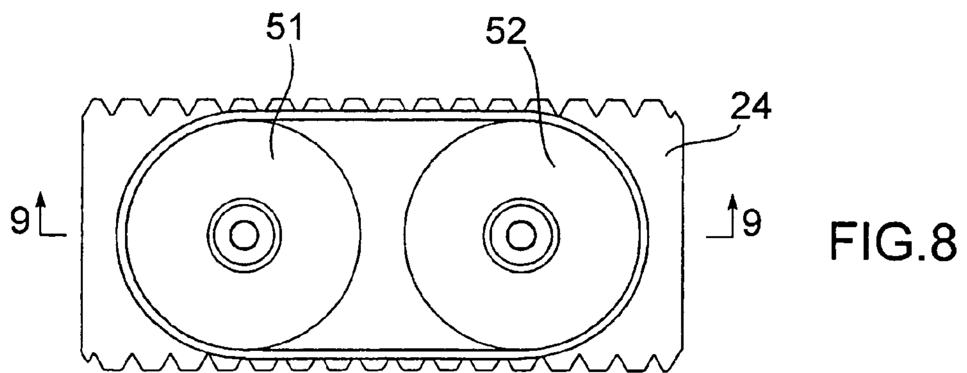
FIG. 8 is a top plan view of the lower half housing shown in FIG. 7.
Figure 9:
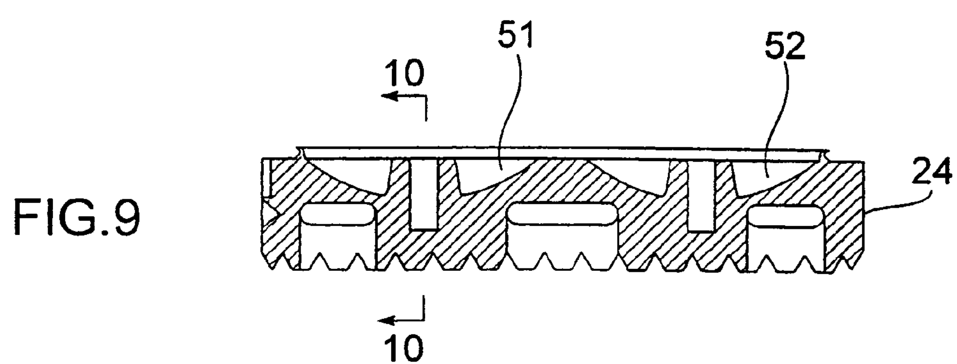
FIG. 9 is a sectional view taken substantially in the plane of line 9—9 in FIG. 8.
Figure 10:
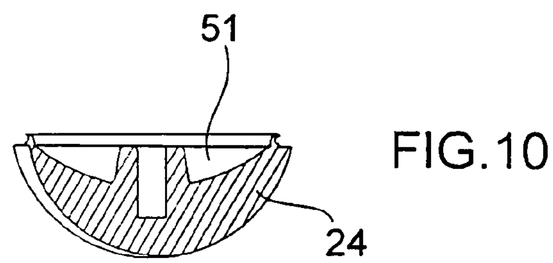
FIG. 10 is a sectional view taken substantially in the plane of line 10—10 in FIG. 9.
Figure 11:
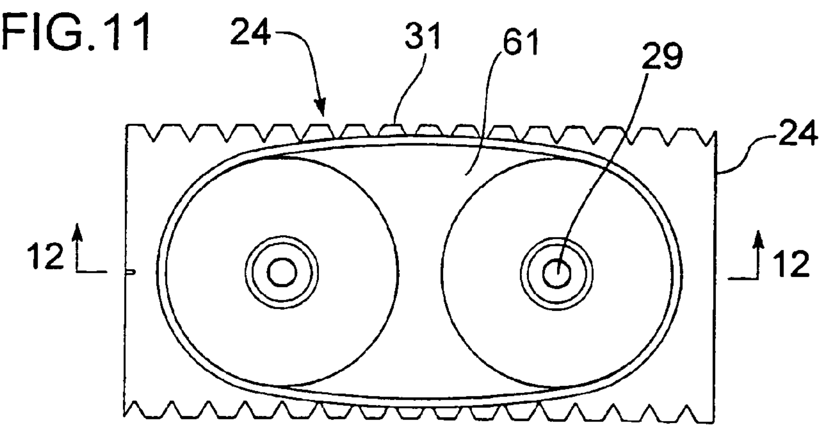
FIG. 11 is a top plan view of a lower half housing similar to FIG. 8 but showing and alternate embodiment of the invention.
Figure 12:
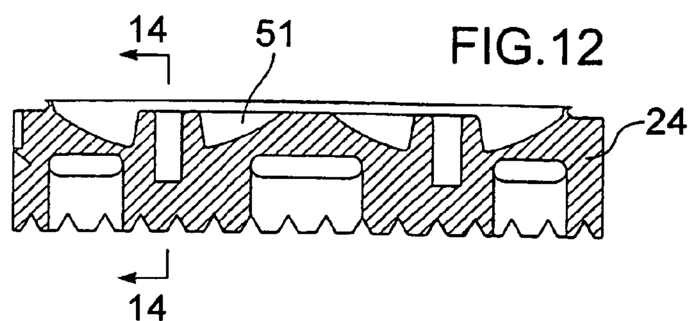
FIG. 12 is a sectional view similar to FIG. 9 but taken substantially in the plane of line 12—12 in FIG. 11.
Figure 13:
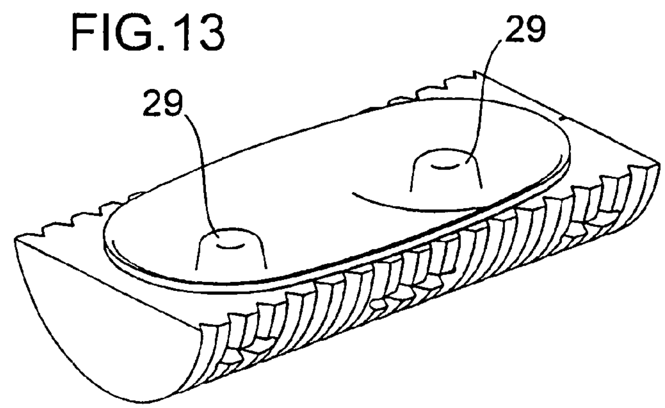
FIG. 13 is an isometric view of the lower half housing shown in FIGS. 11 and 12.
Figure 14:
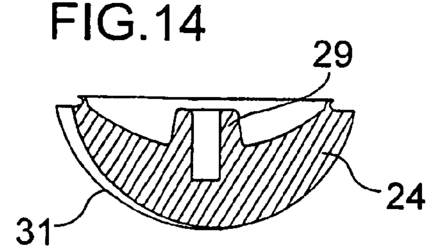
FIG. 14 is a sectional view taken substantially in the plane of line 14—14 in FIG. 12.

To accomplish the objectives set out above, the novel exemplary disc prosthesis 10 includes, as shown in FIGS. 1 and 4, a cylindrical housing 20. The housing 20 includes an upper half housing 22 and a lower half housing 24. In the embodiment showed in FIG. 1, an upper fixator wing 26 is welded or otherwise associated with the upper half housing 22, and a lower fixator wing 28 is similarly welded or otherwise associated with the lower half housing 24. These wings 26, 28 can be used to stabilize the prosthesis to bone, as suggested in U.S. Pat. No. 5,674,296. The wings 26, 28 can be omitted, as suggested in FIGS. 4–14.

As particularly shown in FIGS. 2, 3, 5 and 6, a plurality of resilient, viscoelastic discs 41, 42 are interposed between the upper half housing 22 and the lower half housing 24 to maintain the housing halves separate from one another and to provide for a defined range of motion. Alternatively, the discs 41, 42 may be made of a suitable hydrogel. If desired, generally conical bosses or posts 29 can fit into recesses 33 formed in the discs 41, 42 to provide stability and limitation against excessive motion.

The housing 20 has an exterior surface 30 which bears a screw thread shape 31. This screw thread shape 31 is continuous, and is contiguous from housing half 22 to housing half 24 so that the disc prosthesis can be screwed into a pre-tapped intervertebral space hole formed within between two adjacent vertebrae as, for example, in the human spine. If desired, recesses 35 can be formed to permit bone ingrowth and further stabilization of the device. The housing 20 shape can be that of a right cylinder or it can be conical.

In accordance with one aspect of the invention, this small or thin profile prosthesis 10 can be created by placing more than one ovoid resilient prosthetic discs 41, 42 within a cylindrical housing 20 of metal, ceramic or polymeric material (the housing 20 having been separated into two halves 22, 24 longitudinally). This small device 10 can be implanted in the spine through a small surgical opening. One device 20 containing two or more discs 41, 42 may be used, or by placing two such devices 20 in parallel, each containing two or more ovoid discs in series, a full range of motion of the functional spinal unit (FSU) can be achieved. If the discoid material possesses resilient, viscoelastic properties, with the housing being split or otherwise open on its sides with the internally placed ovoid discs maintaining the separation of the upper and lower housing members, a cushioning effect may also be realized. If desired, a flexible sheath or seal 50 (FIG. 3) can be attached to the housing halves, as by a retaining wire or band, as suggested in U.S. Pat. No. 5,674,296.

As suggested in FIGS. 7–10, each ovoid disc 41, 42 may be surrounded by a concave surface 51, 52 formed or contained within the housing, and contoured to accept the upper and lower surface shape of each of the ovoid discs 41, 42 so that the housing 20 comprising the two or more halves or paired shells 23, 24 may slide and/or rotate over the surface of the discs 41, 42 to provide for joint space separation and motion.

As suggested in FIGS. 11–14, a single recess 61 can be provided to accommodate both discs 41, 42. If desired, posts 29 can be provided to limit disc—housing half relative motion.

As noted above, the exterior surface of the split housing 20 has a threaded formation so that it may be screwed into a pre-tapped hole of appropriate size at an intervertebral disc space. When properly screwed into place, the upper half of the threaded housing engages the cephalad vertebral bone inferior end plate and the other half 24 of the threaded housing engages the opposing superior end plate of the caudal vertebral bone when fully inserted. The ovoid discs 41, 42 and their respective concave surfaces in any one housing unit may be of differing size so as to allow for appropriate spinal column curvature, especially when inserted in the anterior/posterior direction, or they may be the same size in any one housing but differ from the size of the discs in the second housing placed in parallel when inserted from a lateral direction.

The device may be inserted via open or minimally invasive techniques including endoscopy, or by a variety of known surgical approaches where adequate anatomical space is available. Though the prosthesis is inserted as a single threaded cylindrical unit, its final position is such that one half of the housing is left exclusively in contact with the end plate of one vertebral body and the other in the exclusive contact of the opposing vertebral body end plate. The discoid vertebral bodies between the cylindrical housing halves contain two or more concave surfaces, allow movement by providing for sliding and rotating in multiple directions and cushioning in response to physiological loads placed upon them. When cylinders of different size are at used in parallel, intervertebral spacing can be varied to achieve desired vertebrae positional relationships.

We claim:

1. A disc prosthesis comprising, in combination, a cylindrical housing, the housing including an upper half and a lower half and a plurality of resilient, viscoelastic discs interposed between the upper half housing and the lower half housing to maintain the housing halves separate from one another, wherein said discs are ovoid in shape and are of similar size and compressibility.

2. A disc prosthesis according to claim 1 wherein said discs are non-coaxial.

3. A disc prosthesis according to claim 1 wherein each disc is partly surrounded by a concave surface formed within said housing and at least one post extending from the concave surface into a central portion of the corresponding disc.

4. A disc prosthesis according to claim 1 wherein said housing has a threaded exterior surface bearing a screw thread shape.

5. A disc prosthesis according to claim 4 wherein said screw thread is continuous, and is contiguous from housing half to housing half so that the disc prosthesis can be screwed into a pre-tapped intervertebral space hole.

6. A disc prosthesis according to claim 1 wherein recesses are defined in said housing to permit bone ingrowth.

7. A disc prosthesis according to claim 4 including a wing member attached to each of the upper and the lower half housing members, the wings permitting the housing halves to be affixed to spinal vertebrae.

8. A disc prosthesis adapted to be affixed within a human spine, the prosthesis comprising an upper half housing of a cylindrical housing engaging the cephalad vertebral bone inferior end plate; a lower half housing engaging the caudal vertebral bone superior end plate; and a plurality of separate, resilient ovoid discs interposed between the housing halves.

9. A disc prosthesis adapted to be affixed within a human spine, the prosthesis comprising an upper half housing engaging the cephalad vertebral bone inferior end plate; a lower half housing engaging the caudal vertebral bone superior end plate; and a plurality of separate, resilient discs interposed between the housing halves wherein each disc is partly surrounded by a concave surface formed within one of said housing halves.

10. A disc prosthesis according to claim 8 wherein each housing half has a threaded exterior surface.

11. A disc prosthesis comprising, in combination, a hollow cylindrical housing with a substantially circular outer cross-section, the housing including two separate halves and at least one prosthetic disc located between the two housing halves, wherein each housing half is at least partly defined, in its interior, by a concave surface.

12. A plurality of disc prostheses located within a human spine, each prosthesis comprising an upper half housing engaging a bearing surface of a cephalad bone inferior end plate; a lower half housing engaging a caudal vertebral bone superior end plate; and at least one resilient ovoid disc interposed between each of the housing halves, wherein each prosthesis has a threaded exterior surface.

13. A plurality of disc prosthesis according to claim 12 wherein each prosthesis has recesses defined in its exterior surface to permit bone ingrowth.

14. A disc prosthesis comprising:

a cylindrical housing, comprising at least two rigid, confronting and complimentary parts, each having an exterior surface together defining a general continuous thread formation, and each having an interior surface at least a portion of which is concave;

at least one resilient, viscoelastic disc interposed between and contained within the interior surfaces of the housing parts to maintain the housing parts separate from one another but to provide cushioning between the housing parts and to permit limited motion of the housing parts.

15. A disc prosthesis according to claim 14 wherein the housing thread is adapted to engage the bone of adjacent vertebral bodies.

16. A disc prosthesis according to claim 14 including a sheath attached to said housing halves.

17. A disc prosthesis according to claim 14 including a plurality of resilient, viscoelastic discs of different sizes.

18. A disc prosthesis comprising, in combination, a hollow having an outer cylindrical cross-section housing, the housing including two separate halves and at least one prosthetic disc located between the two housing halves, wherein each housing half is at least partly defined by a concave surface and at least one of the housing halves includes a region configured for promoting bony in-growth.

19. The disc prosthesis of claim 18 wherein the region is in the form of a recess.

* * * * *